(12) United States Patent
Bin et al.

(10) Patent No.: US 11,001,574 B2
(45) Date of Patent: May 11, 2021

(54) PROCESS TO OBTAIN A TETRAHYDROISOQUINOLINE DERIVATIVE

(71) Applicant: Medichem S.A., Sant Joan Despí (ES)

(72) Inventors: Zhu Bin, Jiangsu (CN); Rao Lingxiang, Jiangsu (CN); Jordi Puig Serrano, Canet d'Adri (ES); Ernesto Durán López, Castellbisbal (ES)

(73) Assignee: Medichem S.A., Sant Joan Despi (ES)

( * ) Notice: Subject to any disclaimer, the term of this patent is extended or adjusted under 35 U.S.C. 154(b) by 0 days.

(21) Appl. No.: 16/764,795

(22) PCT Filed: Nov. 16, 2018

(86) PCT No.: PCT/EP2018/081565
§ 371 (c)(1),
(2) Date: May 15, 2020

(87) PCT Pub. No.: WO2019/096996
PCT Pub. Date: May 23, 2019

(65) Prior Publication Data
US 2020/0369651 A1   Nov. 26, 2020

(30) Foreign Application Priority Data

Nov. 17, 2017 (EP) ..................... 17382780

(51) Int. Cl.
*C07D 405/06* (2006.01)
*B01J 23/44* (2006.01)
*C07D 217/06* (2006.01)

(52) U.S. Cl.
CPC ............ *C07D 405/06* (2013.01); *B01J 23/44* (2013.01); *C07D 217/06* (2013.01)

(58) Field of Classification Search
CPC .................................................. C07D 405/06
USPC ....................................................... 546/146
See application file for complete search history.

(56) References Cited

FOREIGN PATENT DOCUMENTS

| CN | 106995439 | * | 8/2017 |
| CN | 106995439 A | | 8/2017 |
| WO | WO 2006/125119 A1 | | 11/2006 |
| WO | WO 2009/139817 A2 | | 11/2009 |
| WO | WO 2011/050175 A1 | | 4/2011 |
| WO | WO 2014/018748 A1 | | 1/2014 |

OTHER PUBLICATIONS

International Search Report and Written Opinion of the International Searching Authority dated Jan. 4, 2019 for PCT Application No. PCT/EP2018/081565, 14 pages.
Montalbetti, et al:"Amide bond formation and peptide coupling", Tetrahedron Report No. 740, Nov. 1, 2005; vol. 61, No. 46, pp. 10827-10852, XP055535483.

* cited by examiner

*Primary Examiner* — Patricia L Morris
(74) *Attorney, Agent, or Firm* — Squire Patton Boggs (US) LLP

(57) ABSTRACT

The present invention relates to a process for preparing lifitegrast or a salt thereof, wherein the process comprises hydrogenation of compound II in a mixture comprising at least one solvent selected from the group consisting of acetonitrile, a ketone solvent, an ester solvent and a mixture thereof, preferably acetonitrile.

20 Claims, No Drawings

PROCESS TO OBTAIN A TETRAHYDROISOQUINOLINE DERIVATIVE

This application is a national-phase filing under 35 U.S.C. § 371 of International Application No. PCT/EP2018/081565 (filed on Nov. 16, 2018), which claims the benefit of European Patent Application No. EP 17382780.9 (filed on Nov. 17, 2017).

FIELD OF THE INVENTION

The present invention relates to a novel process to obtain lifitegrast.

BACKGROUND ART

Lifitegrast (Compound I) is the international commonly accepted name for (S)-2-[2-(benzofuran-6-carbonyl)-5,7-dichloro-1,2,3,4-tetrahydroisoquinoline-6-carboxamido]-3-[3-(methylsulfonyl)phenyl]propanoic acid, and has an empirical formula of $C_{29}H_{24}Cl_2N_2O_7S$ and a molecular weight of 615.48 g/mol.

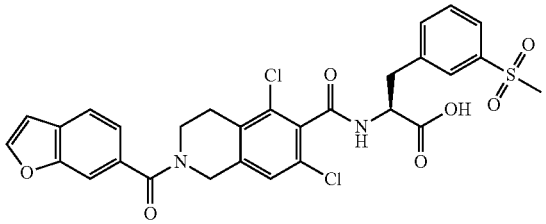

(I)

Lifitegrast is a lymphocyte function-associated antigen-1 (LFA-1) antagonist indicated for the treatment of the signs and symptoms of dry eye disease. Lifitegrast is marketed in the United States under the name Xiidra™ as a 5% ophthalmic solution for the treatment of dry eye disease.

Lifitegrast was first disclosed in patent application WO 2006/125119 A1, but this patent application does not disclose any synthetic procedure for the preparation of lifitegrast.

Patent application WO 2009/139817 A2 discloses a manufacturing process for lifitegrast which comprises transfer hydrogenolysis of an ester of formula II with a palladium catalyst and a source of protons, such as formic acid. The process is summarized in Scheme 1, below.

Scheme 1

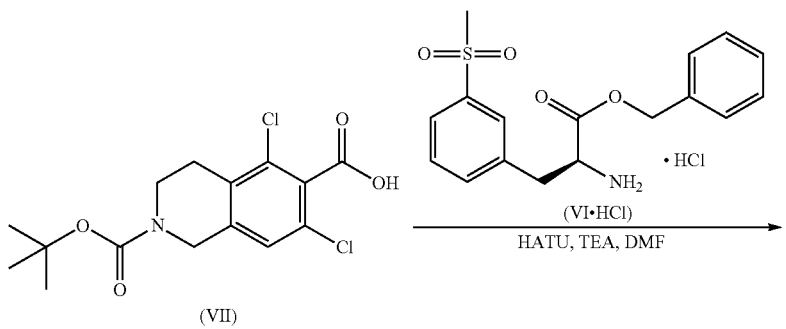

(VII)

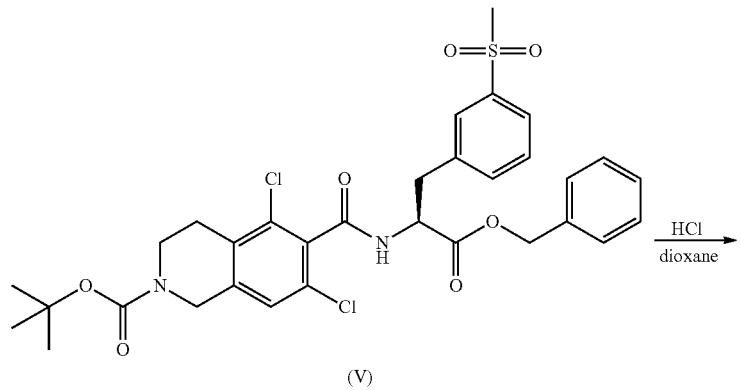

(V)

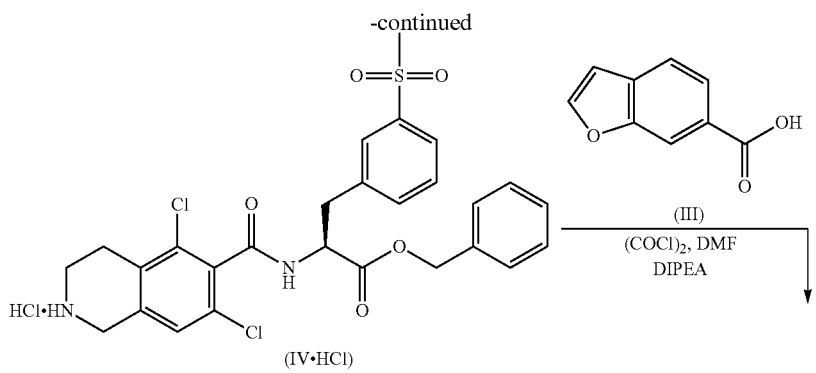

Namely, patent application WO 2009/139817 A2 discloses that compound VI is coupled with compound VII, using HATU and triethylamine in DMF, to obtain compound V in quantitative yield. Deprotection with hydrogen chloride in dioxane yields compound IV in form of its hydrochloride salt in 97.4% yield. Compound III is treated with oxalyl chloride and a catalytic amount of N,N-dimethylformamide, and the resulting acid chloride is added to a solution of compound IV and diisopropylethylamine in dichloromethane, to give compound II in quantitative yield. The benzyl ester of compound II is removed by transfer hydrogenolysis in the presence of 10% palladium on carbon, using formic acid and triethylamine in a 5:1 mixture of methanol:tetrahydrofuran, to produce compound I in 95% yield and 97% purity. The patent application also discloses that lifitegrast is produced with a much higher optical purity (98.5% S enantiomer) than the optical purity obtained (79-94.5% S enantiomer) by hydrolysis of a corresponding methyl ester.

Patent application WO 2011/050175 A1 discloses alternative synthetic strategies to obtain lifitegrast, comprising reacting compound II with a base in a solvent to accomplish the base-catalyzed saponification of compound II, or with an acid in a solvent to accomplish the acid-catalyzed hydrolysis of compound II. Namely, patent application WO 2011/050175 A1 discloses the reaction of compound II with sodium hydroxide in a mixture of dioxane and water, to give crude lifitegrast as a foam having 95% purity and 94.8% enantiomeric excess. Similarly, patent application WO 2014/018748 A1 discloses the reaction of compound II with sodium hydroxide, in the presence of tetrabutylammonium hydroxide, in a mixture of acetone and water, to give crude lifitegrast with 88% yield.

The procedures disclosed in the literature are not suitable for the manufacture of lifitegrast at industrial scale. Namely, the processes involving hydrolysis of the benzyl ester (compound II) under basic conditions are known to yield higher amounts of the undesired R enantiomer of lifitegrast. In this sense, the literature discloses a lower optical purity for the lifitegrast as obtained by hydrolysis with sodium hydroxide in a mixture of dioxane and water (94.8% enantiomeric excess), as disclosed in patent application WO 2011/050175 A1, than for the lifitegrast as obtained by transfer hydrogenolysis of compound II (98.5% S enantiomer, which is equivalent to 97.0% enantiomeric excess), as disclosed in patent application WO 2009/139817 A2. On the other hand, the hydrolysis of the benzyl ester (compound II) under acidic conditions, as suggested in patent application WO 2011/050175 A1, is expected to yield lifitegrast containing a higher amount of impurities since patent application WO 2014/018748 A1 discloses that local pH of less than about 1 should be avoided as to reduce racemization and/or hydrolysis of lifitegrast. Additionally, the authors of the present invention have found that the transfer hydrogenolysis of compound II using 10% palladium on carbon, formic acid and triethylamine in a 5:1 mixture of methanol:tetrahydrofuran, as disclosed in patent application WO 2009/139817 A2, can yield lifitegrast with a high content of dechlorinated impurities A and/or B and/or C.

Impurity A

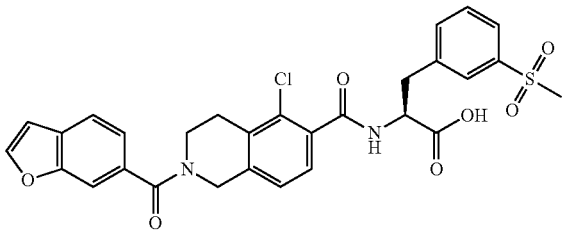

-continued

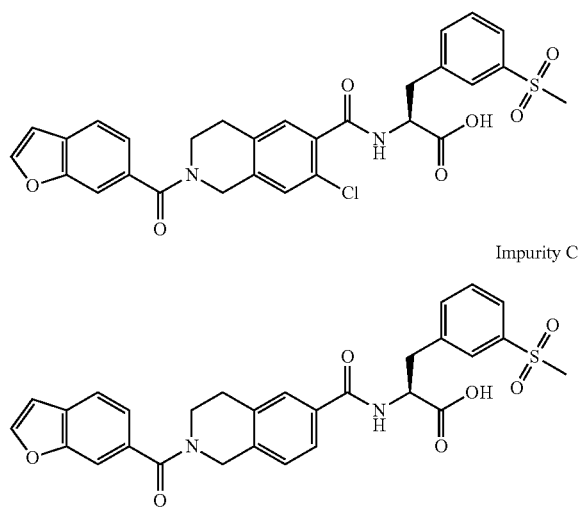

Impurity B

Impurity C

Moreover, the synthetic process of compound II disclosed in WO 2009/139817 A2 involves serious drawbacks with regards to its industrial applicability. Namely, the coupling between compounds VI and VII involves the use of HATU, which is an extremely expensive coupling reagent. Additionally, the deprotection of compound V involves the use of 1,4-dioxane as solvent, which is a probable human carcinogen, and the coupling between compounds III and IV involves the use of highly toxic dichloromethane as solvent.

Consequently, there is an unmet need for improved synthetic processes for preparing lifitegrast which avoid the drawbacks of the processes disclosed in the literature and are suitable for the manufacture of lifitegrast at industrial scale.

BRIEF SUMMARY OF THE INVENTION

The present invention is related to a process for preparing lifitegrast.

The process of the present invention provides lifitegrast of high purity. Particularly, the process of the present invention provides lifitegrast having a low content of dechlorinated impurities A and/or B and/or C and also a low content of the undesired R enantiomer of lifitegrast.

DETAILED DESCRIPTION OF THE INVENTION

The present invention is related to a process for preparing lifitegrast.

A first aspect of the present invention provides a process for preparing lifitegrast or a salt thereof, the process comprising hydrogenation of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) in a mixture comprising at least one solvent selected from the group consisting of acetonitrile, a ketone solvent, an ester solvent and a mixture thereof, preferably acetonitrile.

The ketone solvent in the hydrogenation of compound II is a compound of formula $R_1COR_2$, wherein $R_1$ and $R_2$ are independently $(C_1-C_8)$alkyl, $(C_6-C_{12})$aryl and $(C_6-C_{12})$aryl-$(C_1-C_8)$alkyl. The ketone solvent in the hydrogenation of compound II is preferably selected from the group consisting of acetone, methyl butyl ketone, methyl ethyl ketone, methyl isobutyl ketone, methyl isopropyl ketone and a mixture thereof.

The ester solvent in the hydrogenation of compound II is a compound of formula $R_3COOR_4$, wherein $R_3$ and $R_4$ are independently $(C_1-C_8)$alkyl, $(C_6-C_{12})$aryl and $(C_6-C_{12})$aryl-$(C_1-C_8)$alkyl. The ester solvent in the hydrogenation of compound II is preferably selected from the group consisting of butyl acetate, ethyl acetate, ethyl formate, isobutyl acetate, isopropyl acetate, methyl acetate, methyl formate, propyl acetate and a mixture thereof.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl and tert-butyl.

The term "$(C_6-C_{12})$aryl" refers to an aromatic known ring system comprising one or more rings and from 6 to 12 ring members, wherein all the ring members comprise carbon atoms. Examples of $(C_6-C_{12})$aryl include phenyl and naphthalene. The term "known ring system" as used herein refers to a ring system which is chemically feasible and is known in the art and so intends to exclude those ring systems that are not chemically possible.

The groups $(C_1-C_8)$alkyl and $(C_6-C_{12})$aryl as defined in the present invention may be unsubstituted or substituted as described herein, being the substituents placed on any available position.

In a preferred embodiment of the present invention, the hydrogenation of compound II is performed in a solvent comprising acetonitrile.

The hydrogenation of compound II comprises the addition of hydrogen from molecular hydrogen ($H_2$), or from a hydrogen donor or from mixtures thereof, to compound II. The hydrogen donor is preferably selected from the group comprising formic acid or a salt thereof, hypophosphorous acid or a salt thereof, phosphorous acid or a salt thereof, isopropanol, hydrazine, 1,3-cyclohexadiene, 1,2-dihydronaphthalene, 9,10-dihydroanthracene and a mixture thereof.

In a preferred embodiment of the present invention, the hydrogenation of compound II comprises the use of formic acid or a salt thereof as a hydrogen donor. The salt of formic acid is preferably selected from the group comprising an alkaline salt of formic acid, an earth alkaline salt of formic acid, an ammonium salt of formic acid and a mixture thereof. The alkaline salt of formic acid is preferably selected from the group comprising lithium formate, sodium formate, potassium formate, cesium formate and a mixture thereof. The earth alkaline salt of formic acid is preferably selected from the group comprising magnesium formate, calcium formate and a mixture thereof. The ammonium salt of formic acid is preferably selected from the group comprising ammonium formate, trimethylammonium formate, triethylammonium formate, diisopropylethylammonium formate, N-methylmorpholinium formate, tetramethylammonium formate, tetraethylammonium formate, tetrabutylammonium formate and a mixture thereof. The ammonium salt of formic acid can be loaded in salt form to the reaction, or can be prepared in situ by reaction between formic acid and the corresponding base. In a particularly preferred embodiment of the present invention, the hydrogenation donor in the hydrogenation of compound II is triethylammonium formate. Particularly, the hydrogenation of compound II comprises the use of triethylammonium formate prepared in situ by reaction between formic acid and triethylamine.

The hydrogenation of compound II comprises the addition of hydrogen to compound II in the presence of a catalyst. The catalyst can be homogeneous or heterogeneous. The catalyst typically comprises a transition metal catalyst. The transition metal catalyst is preferably selected from the group comprising palladium, platinum, nickel, iron and rhodium catalysts and mixtures thereof.

In a preferred embodiment of the present invention, the hydrogenation of compound II comprises the addition of hydrogen to compound II in the presence of palladium, preferably palladium (0) on charcoal.

In a preferred embodiment of the present invention, the hydrogenation is a transfer hydrogenolysis catalyzed by palladium and in the presence of formic acid or a salt thereof as a hydrogen donor.

The hydrogenation of compound II can optionally be performed in the presence of a chloride salt. The chloride salt is preferably selected from the group comprising an alkaline chloride, an earth alkaline chloride, an ammonium chloride, a phosphonium chloride and a mixture thereof. The alkaline chloride is preferably selected from the group comprising lithium chloride, sodium chloride, potassium chloride, cesium chloride and a mixture thereof. The earth alkaline chloride is preferably selected from the group comprising magnesium chloride, calcium chloride and a mixture thereof. The ammonium chloride is preferably selected from the group comprising tetramethylammonium chloride, tetraethylammonium chloride, tetrabutylammonium chloride, cetyltriethylammonium chloride, butyltrimethylammonium chloride, hexadecyltrimethylammonium chloride and a mixture thereof. The phosphonium chloride is preferably selected from the group comprising tetramethylphosphonium chloride, tetrabutylphosphonium chloride and a mixture thereof.

In a preferred embodiment of the present invention, the hydrogenation of compound II is performed in the presence of an ammonium chloride salt, preferably tetrabutylammonium chloride.

In a preferred embodiment of the present invention, the hydrogenation of compound II is carried out at a temperature of from about 0° C. to about 50° C., preferably from about 20° C. to about 45° C., more preferably from about 20° C. to about 25° C., from about 25° C. to about 30° C., from about 30° C. to about 35° C., from about 35° C. to about 40° C., or from about 40° C. to about 45° C.

The hydrogenation process for preparing lifitegrast of the present invention shows an improved selectivity for the debenzylation reaction over the dechlorination by-process than the hydrogenation process of compound II described in the literature. Namely, the hydrogenation of compound II using formic acid and triethylamine in a 5:1 mixture of methanol:tetrahydrofuran yields lifitegrast containing high amounts of dechlorinated impurities A and/or B and/or C when the debenzylation reaction is carried out to completion, i.e. when the amount of unreacted compound II in the reaction mixture is lower than 5% as determined by thin layer chromatography (TLC) or HPLC analysis. Contrarily, the hydrogenation process for preparing lifitegrast of the present invention yields lifitegrast containing substantially lower amounts of dechlorinated impurities A and/or B when the debenzylation reaction is carried out to completion and, consequently, the double dechlorinated impurity C is less likely to be found. This allows achieving a better conversion of compound II into lifitegrast without forming a high amount of undesirable by-products, which is preferable for the manufacture of lifitegrast at industrial scale.

On the other hand, the process for preparing lifitegrast of the present invention also prevents the formation of the hydrolysis and racemization by-products which are formed under the hydrolysis conditions (acidic or basic) of compound II disclosed in the literature for the synthesis of lifitegrast. Particularly, the process for preparing lifitegrast of the present invention yields lifitegrast containing not more than 0.15% of enantiomer R of lifitegrast, preferably not more than 0.10% of enantiomer R of lifitegrast, more preferably not more than 0.05% of enantiomer R of lifitegrast, even more preferably no detectable amounts of enantiomer R of lifitegrast, as determined by chiral HPLC analysis.

In another embodiment of the present invention, the process comprises:
(a) reacting benzofuran-6-carboxylic acid (compound III) or a salt thereof with 1,1'-carbonyldiimidazole (CDI) to obtain an activated derivative of compound III; and
(b) reacting the activated derivative of compound III of step (a) with benzyl (S)-2-(5,7-dichloro-1,2,3,4-tetrahydroisoquinoline-6-carboxamido)-3-[3-(methylsulfonyl)phenyl]propanoate (compound IV) or a salt thereof, to obtain compound II.

In a preferred embodiment of the present invention, the reaction to obtain compound II is performed in a solvent selected from the group consisting of butyl acetate, ethyl acetate, ethyl formate, isobutyl acetate, isopropyl acetate, methyl acetate, methyl formate, propyl acetate, dimethylsulfoxide, N,N-dimethylformamide, N,N-dimethylacetamide and a mixture thereof, preferably in a mixture comprising ethyl acetate and dimethylsulfoxide.

In a preferred embodiment of the present invention, the reaction to obtain compound II is performed at a temperature of from about 0° C. to about 50° C., preferably from about 20° C. to about 45° C.

In another embodiment of the present invention, the process comprises deprotecting benzyl (S)-2-[2-(tert-butoxycarbonyl)-5,7-dichloro-1,2,3,4-tetrahydroisoquinoline-6-carboxamido]-3-[3-(methylsulfonyl)phenyl]propanoate (compound V) to obtain compound IV.

In a preferred embodiment of the present invention, the deprotection of compound V is performed using hydrogen chloride in a solvent selected from the group consisting of butyl acetate, ethyl acetate, ethyl formate, isobutyl acetate, isopropyl acetate, methyl acetate, methyl formate, propyl acetate and a mixture thereof, preferably butyl acetate.

In a preferred embodiment of the present invention, the deprotection of compound V is performed at a temperature of from about 0° C. to about 50° C., preferably from about 15° C. to about 30° C., more preferably from about 20° C. to about 25° C.

In another embodiment of the present invention, the process comprises:
(c) reacting 2-(tert-butoxycarbonyl)-5,7-dichloro-1,2,3,4-tetrahydroisoquinoline-6-carboxylic acid (compound VII) or a salt thereof with oxalyl chloride to obtain an activated derivative of compound VII; and
(d) reacting the activated derivative of compound VII of step (c) with benzyl (S)-2-amino-3-[3-(methylsulfonyl)phenyl]propanoate (compound VI) or a salt thereof, to obtain compound V.

In a preferred embodiment of the present invention, the reaction to obtain compound V is performed in a solvent selected from the group consisting of butyl acetate, ethyl acetate, ethyl formate, isobutyl acetate, isopropyl acetate, methyl acetate, methyl formate, propyl acetate, dimethylsulfoxide, N,N-dimethylformamide, N,N-dimethylacetamide and a mixture thereof, preferably in a mixture comprising butyl acetate and N,N-dimethylformamide.

In a preferred embodiment of the present invention, the reaction to obtain compound V is performed at a temperature of from about 0° C. to about 50° C., preferably from about 0° C. to about 30° C.

In another aspect of the present invention, lifitegrast is obtained by following the route of synthesis depicted in Scheme 2.

Another aspect of the present invention provides lifitegrast obtained by a process comprising hydrogenation of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) in a mixture comprising at least one solvent selected from the group consisting of acetonitrile, a ketone solvent, an ester solvent and a mixture thereof, preferably acetonitrile.

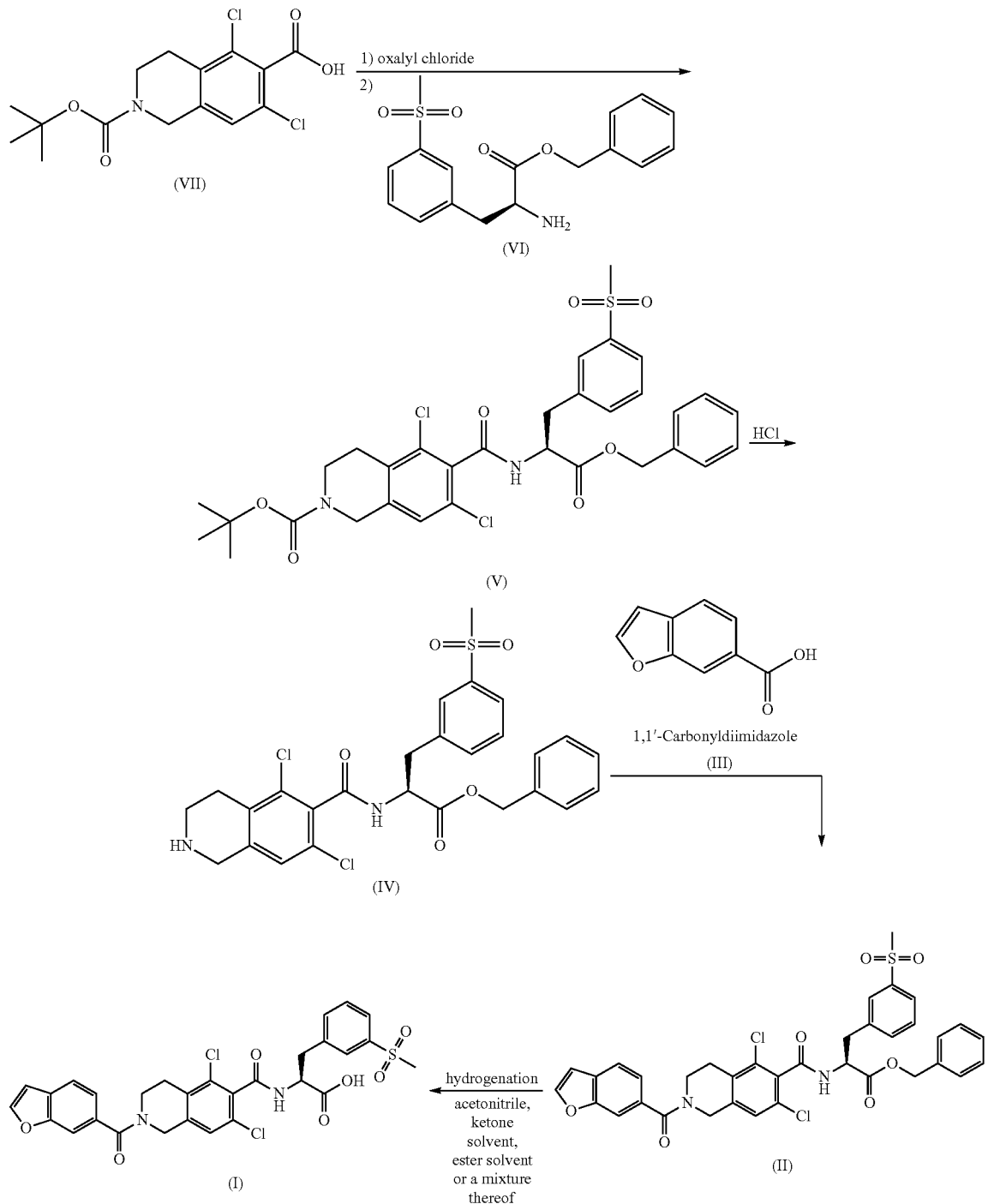

In a preferred embodiment of the present invention, the obtained lifitegrast contains not more than 0.15% of enantiomer R of lifitegrast, preferably not more than 0.10% of enantiomer R of lifitegrast, more preferably not more than 0.05% of enantiomer R of lifitegrast, even more preferably no detectable amounts of enantiomer R of lifitegrast, as determined by chiral HPLC analysis.

Another aspect of the present invention provides a pharmaceutical formulation comprising lifitegrast obtained by a process comprising hydrogenation of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) in a mixture comprising at least one solvent selected from the group consisting of acetonitrile, a ketone solvent, an ester solvent and a mixture thereof, preferably acetonitrile.

In a preferred embodiment of the present invention, the pharmaceutical formulation comprises a sterile solution. The sterile solution may be prepared by dissolving lifitegrast in a sterile aqueous solution such as physiological saline, buffering solution. If desired, additives ordinarily used can be added.

In a particularly preferred embodiment of the present invention, the pharmaceutical formulation comprises an isotonizing agent such as sodium chloride; a buffering agent such as sodium monohydrogenphosphate or sodium dihydrogenphosphate; an antioxidant such as a thiosulfate salt, a metabisulfite salt, esters of gallic acid, butylated hydroxyanisole, green tea extract, uric acid, cysteine, pyruvate, nordihydroguaiaretic acid, ascorbic acid or salts thereof, ascorbyl glucosamine, vitamin E or derivatives thereof, retinoids, sodium citrate, sodium sulfite, lycopene, anthocyanids, bioflavinoids, superoxide dismutase, glutathione peroxidase, butylated hydroxytoluene, indole-3-carbinol, pycnogenol, melatonin, sulforaphane, pregnenolone, lipoic acid and 4-hydroxy-5-methyl-3[2H]-furanone, preferably sodium thiosulfate; sodium hydroxide and/or hydrochloric acid (used to adjust pH) and water for injection.

Another aspect of the present invention provides a pharmaceutical formulation comprising lifitegrast obtained by a process comprising hydrogenation of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) in a mixture comprising at least one solvent selected from the group consisting of acetonitrile, a ketone solvent, an ester solvent and a mixture thereof, preferably acetonitrile, for use in the treatment of dry eye disease.

The term "about" when used in the present invention preceding a number and referring to it, is meant to designate any value which lies within the range defined by the number ±10% of its value, preferably a range defined by the number ±5% of its value, more preferably a range defined by the number ±2% of its value, still more preferably a range defined by the number ±1% of its value. For example "about 10" should be construed as meaning within the range of 9 to 11, preferably within the range of 9.5 to 10.5, more preferably within the range of 9.8 to 10.2, and still more preferably within the range of 9.9 to 10.1.

EXPERIMENTAL EXAMPLES

HPLC

The chromatographic separation was carried out using a Waters Symmetry shield RP18, 5 μm (4.6×250 mm) column, at 25° C.

The mobile phase A was prepared by dissolving 1.09 g of monobasic potassium phosphate in 1000 mL of HPLC gradient grade water and adjusting the pH to 2.0 with 85% phosphoric acid.

The mobile phase B was HPLC gradient grade acetonitrile.

The chromatograph was programmed as follows: Initial 0-10 min. isocratic 80% mobile phase A, 10-25 min. linear gradient to 60% mobile phase A, 25-35 min. linear gradient to 40% mobile phase A, 35-45 min. isocratic 40% mobile phase A, 45-55 min. linear gradient to 80% mobile phase A, 55-65 min. isocratic 80% mobile phase A.

The chromatograph was equipped with a UV detector operating at 220 nm. The flow rate was 1.0 mL/min.

Test samples were prepared by dissolving about 25 mg of sample to 50.0 mL with water/acetonitrile 50:50 (v/v) mixture. 10 μL of the test samples were injected.

Chiral HPLC

The chromatographic separation was carried out using a ChiralPak ZWIX(+), 3 μm (4.0×150 mm) column, at 25° C.

The mobile phase was a mixture of HPLC gradient grade acetonitrile, formic acid and diethylamine (992.9/1.9/5.2) (v/v/v).

The chromatograph was equipped with a UV detector operating at 254 nm. The flow rate was 0.4 mL/min.

Test samples were prepared by dissolving about 25 mg of sample to 10.0 mL with methanol. 8 μL of the test samples were injected. The chromatograph was run for 20 minutes.

Example 1

Preparation of Hydrochloride Salt of Compound IV 34.6 g (0.10 mol) of 2-(tert-butoxycarbonyl)-5,7-dichloro-1,2,3,4-tetrahydroisoquinoline-6-carboxylic acid (compound VII) and 12.1 mL (0.11 mol) of N-methylmorpholine were suspended in 350 mL of butyl acetate under nitrogen atmosphere. 0.05 mL of N,N-dimethylformamide were added, and the resulting suspension was cooled to 0-5° C. 13.7 mL (0.16 mol) of oxalyl chloride were added, and the mixture was stirred at 0-5° C. for 2 hours. The resulting mixture was partially concentrated under vacuum to give 200 g of a solution, which was diluted with 150 mL of fresh butyl acetate and added over a solution of 36.98 g (0.10 mol) of benzyl (S)-2-amino-3-[3-(methylsulfonyl)phenyl]propanoate (compound VI) and 33.0 mL (0.30 mol) of N-methylmorpholine in 350 mL of butyl acetate at 20-25° C., and the mixture was stirred for 18 hours at this temperature. The resulting mixture was extracted with 1 L of 0.5 M hydrochloric acid, 500 mL of saturated aqueous sodium bicarbonate and 500 mL of deionized water, in sequence. The organic phase was partially concentrated under reduced pressure to give 220 g of a solution of benzyl (S)-2-[2-(tert-butoxycarbonyl)-5,7-dichloro-1,2,3,4-tetrahydroisoquinoline-6-carboxamido]-3-[3-(methylsulfonyl)phenyl]propanoate (compound V) in butyl acetate, which was diluted with 400 mL of fresh butyl acetate, and the mixture was stirred at 20-25° C. 600 mL of a 2 M solution of hydrogen chloride in butyl acetate were added, and the resulting suspension was stirred at 20-25° C. for 1 hour. The solid was filtered and washed with 600 mL of ethyl acetate to give 54.0 g of crude hydrochloride salt of benzyl (S)-2-(5,7-dichloro-1,2,3,4-tetrahydroisoquinoline-6-carboxamido)-3-[3-(methylsulfonyl) phenyl]propanoate (compound IV).

Example 2

Purification of Hydrochloride Salt of Compound IV

Crude hydrochloride salt of benzyl (S)-2-(5,7-dichloro-1,2,3,4-tetrahydroisoquinoline-6-carboxamido)-3-[3-(methylsulfonyl)phenyl]propanoate (compound IV) as obtained in Example 1 was suspended in 20 volumes of isopropanol, and the resulting suspension was stirred at reflux temperature for 1 hour. After cooling to 20-25° C., the solid was filtered and dried under vacuum to yield purified hydrochloride salt of benzyl (S)-2-(5,7-dichloro-1,2,3,4-tetrahydroisoquinoline-6-carboxamido)-3-[3-(methylsulfonyl)phenyl]propanoate (compound IV) as a white to yellowish solid.

Example 3

Preparation of compound II.

16.05 g (0.10 mol) of benzofuran-6-carboxylic acid (compound III) were added over a suspension of 16.05 g (0.10 mol) of 1,1'-carbonyldiimidazole in 400 mL of ethyl acetate at 20-25° C., under nitrogen atmosphere. The mixture was stirred at 20-25° C. for 1 hour, and the resulting solution was added over a mixture of 53.8 g (0.09 mol) of crude hydrochloride salt of benzyl (S)-2-(5,7-dichloro-1,2,3,4-tetrahydroisoquinoline-6-carboxamido)-3-[3-(methylsulfonyl)phenyl]propanoate (compound IV) as obtained in Example 1 and 37.6 mL (0.22 mol) of N,N-diisopropylethylamine in a mixture of 200 mL of ethyl acetate and 55 mL of dimethylsulfoxide at 20-25° C. The resulting mixture was stirred at this temperature for 18 hours. 1.05 L of 0.5 M hydrochloric acid and 500 mL of ethyl acetate were added. The organic phase was extracted, washed with 2×500 mL of 4% (w/w) aqueous sodium bicarbonate and with 500 mL of deionized water, in sequence. The organic layer was concentrated to dryness under reduced pressure, to give 63.1 g of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as a yellowish solid.

Comparative Examples 1-2

Preparation of Lifitegrast

Mixtures of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 3, formic acid, triethylamine and 10% (w/w) palladium on charcoal (see amounts in Table 1) were suspended in the corresponding solvent and stirred at the temperatures indicated in Table 1, under nitrogen atmosphere. The amount of unreacted compound II was monitored to be below 5% by TLC. After the indicated stirring time, aliquots of the reaction mixtures were filtered and the resulting solutions were analyzed by HPLC.

TABLE 1

| Comparative Example | 10% Pd/C (w/w) | HCOOH (equiv.) | TEA (equiv.) | Solvent (volumes) | Temp. (° C.) | Time (h) | Unreacted compound II (HPLC, area %) | Dechlorinated impurities A and B (HPLC, total area %) |
| --- | --- | --- | --- | --- | --- | --- | --- | --- |
| 1 | 20% | 10 eq. | 10 eq. | MeOH/THF 5:1 60 vols. | 35-40 | 5 | n.d. | 11% |
| 2 | 5% | 10 eq. | 10 eq. | THF 20 vols. | 25-30 | 1 | n.d. | 30% |

Weight of catalyst (5% or 20%) corresponds to weight of wet (about 50% of water), 10% (w/w) palladium on charcoal with respect to weight of compound II; eq.: equivalents with respect to compound II; MeOH: methanol; THF: tetrahydrofuran; vols.: volumes of solvent with respect to weight of compound II; n.d.: not detected.

Examples 4 to 10

Preparation of Lifitegrast

Mixtures of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 3, formic acid, added base and 10% (w/w) palladium on charcoal (see amounts in Table 2) were suspended in the corresponding solvent and stirred at the temperatures indicated in Table 2, under nitrogen atmosphere. The amount of unreacted compound II was monitored to be below 5% by TLC. After the indicated stirring time, aliquots of the reaction mixtures were filtered and the resulting solutions were analyzed by HPLC.

TABLE 2

| Example 10: Chiral purity (chiral HPLC): 99.92%. | | | | | | | | |
| --- | --- | --- | --- | --- | --- | --- | --- | --- |
| Example | 10% Pd/C (w/w) | HCOOH (equiv.) | Added base (equiv.) | Solvent (volumes) | Temp. (° C.) | Time (h) | Unreacted compound II (HPLC, area %) | Dechlorinated impurities A and B (HPLC, total area %) |
| 4 | 5% | 10 eq. | TEA 10 eq. | EtOAc 20 vols. | 25-30 | 5 | n.d. | 0.77% |
| 5 | 5% | 10 eq. | TEA 10 eq. | iPrOAc 20 vols. | 25-30 | 6 | 0.6% | 1.0% |
| 6 | 5% | 10 eq. | DIPEA 10 eq. | EtOAc 20 vols. | 25-30 | 2 | n.d. | 1.9% |

TABLE 2-continued

Example 10: Chiral purity (chiral HPLC): 99.92%.

| Example | 10% Pd/C (w/w) | HCOOH (equiv.) | Added base (equiv.) | Solvent (volumes) | Temp. (° C.) | Time (h) | Unreacted compound II (HPLC, area %) | Dechlorinated impurities A and B (HPLC, total area %) |
|---|---|---|---|---|---|---|---|---|
| 7 | 5% | 10 eq. | TEA 10 eq. | iBuOAc 20 vols. | 25-30 | 23 | 1.5% | 0.76% |
| 8 | 5% | 10 eq. | TEA 10 eq. | BuOAc 20 vols. | 20-25 | 5 | n.d. | 0.70% |
| 9 | 5% | 3 eq. | TEA 5 eq. | Acetone 20 vols. | 20-25 | 24 | 0.07% | 0.41% |
| 10 | 5% | 3 eq. | TEA 7 eq. | Acetonitrile 20 vols. | 20-25 | 48 | 4.8% | 0.26% |

Weight of catalyst (5% or 20%) corresponds to weight of wet (about 50% of water), 10% (w/w) palladium on charcoal with respect to weight of compound II; eq.: equivalents with respect to compound II; TEA: triethylamine; DIPEA: N,N-diisopropylethylamine; EtOAc: ethyl acetate; iPrOAc: isopropyl acetate; iBuOAc: isobutyl acetate; BuOAc: butyl acetate; vols.: volumes of solvent with respect to weight of compound II; n.d.: not detected.

Example 11

Preparation of Lifitegrast 28.2 g (40 mmol) of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 3 and 1.42 g of 10% palladium on charcoal type 452 (Johnson Matthey) were suspended in 560 mL of acetonitrile, under nitrogen atmosphere. To the resulting suspension were added 4.5 mL (120 mmol, 3 equivalents) of formic acid and 28.0 mL (200 mmol, 5 equivalents) of triethylamine. The suspension was heated to 30-35° C. and stirred at this temperature for 6 hours. Amount of unreacted compound II was below 5% by TLC. The suspension was filtered and the solid was washed with 30 mL of acetonitrile. The filtrate was concentrated to dryness under vacuum and the residue was dissolved in 500 mL of ethyl acetate. After distilling 100 g of solvent, 400 mL of deionized water were added and pH was adjusted to 3-4 with hydrochloric acid. After stirring for 30 minutes at 25-30° C., the organic layer was extracted. 400 mL of 2.5% (w/w) aqueous sodium bicarbonate were added and the mixture was stirred for 30 minutes at 25-30° C. The aqueous layer was extracted and the organic phase was washed with 100 mL of deionized water. The aqueous phases were combined and cooled to 5-10° C. pH was adjusted to 3-4 with hydrochloric acid. The resulting suspension was stirred at 5-10° C. for 30 minutes. The solid was filtered, washed with 2×50 mL of deionized water and dried under vacuum to give 20.4 g of crude lifitegrast. Dechlorinated impurities A and B (HPLC, total area %): 0.16%. XRPD: Amorphous solid.

Example 12

Purification of Lifitegrast 2.0 g of crude lifitegrast as obtained in Example 11 were suspended in 20 mL of acetonitrile under nitrogen atmosphere. The suspension was heated to reflux temperature, stirred for 30 minutes at this temperature, and cooled down to 25-30° C. The solid was filtered and washed with 5 mL of acetonitrile to give 1.74 g of purified lifitegrast. Dechlorinated impurities A and B (HPLC, total area %): 0.13%. XRPD: Form I (Channel Hydrate) as disclosed in patent application WO 2014/018748 A1.

Example 13

Purification of Lifitegrast 1.53 g of purified lifitegrast as obtained in Example 12 were suspended in 30 mL of acetonitrile under nitrogen atmosphere. The suspension was heated to reflux temperature, stirred for 30 minutes at this temperature, and cooled down to 25-30° C. The solid was filtered and washed with 5 mL of acetonitrile to give 1.28 g of purified lifitegrast. Purity (HPLC): 99.7%. Dechlorinated impurities A and B (HPLC, total area %): 0.10%.

Example 14

Purification of Lifitegrast

Crude lifitegrast as obtained in Example 11 was suspended in 30 volumes of acetonitrile under nitrogen atmosphere. The suspension was heated to reflux temperature, stirred for 30 minutes at this temperature, and cooled down to 25-30° C. The solid was filtered to give purified lifitegrast. Enantiomeric excess (chiral HPLC): 100%.

Example 15

Preparation of Lifitegrast 0.71 g (1.0 mmol) of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 3 and 0.04 g of 10% palladium on charcoal type 452 (Johnson Matthey) were suspended in 14.2 mL of acetonitrile, under nitrogen atmosphere. To the resulting suspension were added 0.11 mL (3.0 mmol, 3 equivalents) of formic acid, 0.70 mL (5.0 mmol, 5 equivalents) of triethylamine and 0.14 g (0.5 mmol, 0.5 equivalents) of tetrabutylammonium chloride. The suspension was heated to 40° C. and stirred at this temperature for 4.5 hours. Amount of unreacted compound II was below 5% by TLC. The suspension was filtered and the solid was washed with 3 mL of acetonitrile. The filtrate was concentrated to dryness under vacuum and the residue was dissolved in 15 mL of ethyl acetate. The solution was washed with 15 mL of deionized water. Then, 15 mL of 4% (w/w) aqueous sodium bicarbonate were added. The aqueous layer was extracted and pH was adjusted to 3-4 with hydrochloric acid. The resulting suspension was stirred at 5-10° C. for 30 minutes. The solid was filtered and dried under vacuum to give crude lifitegrast. Dechlorinated impurities A and B (HPLC, total area %): 0.30%.

Example 16

Preparation of Lifitegrast 7.8 g (11.05 mmol) of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 3 were dissolved in 15.6 mL of acetonitrile, under nitrogen atmosphere. The resulting solution was cooled to 3° C. 54.6 mL of 35% hydrochloric acid were added. The mixture was heated to 20-25° C. and stirred at this temperature for 19.5 hours. Amount of unreacted compound II was below 5% by TLC. The mixture was added over 70 mL of deionized water. The resulting suspension was stirred at 20° C. for 30 minutes. The solid was filtered and washed with 40 mL of deionized water. The solid was dissolved in 117 mL of ethyl acetate. The solution was washed with 54.6 mL of deionized water. The aqueous layer was extracted with 40 mL of ethyl acetate. The organic phases were combined and washed with 40 mL of deionized water. 54.6 mL of 4% (w/w) aqueous sodium bicarbonate were added. The aqueous layer was extracted and washed with 40 mL of ethyl acetate. The aqueous solution was treated with 0.39 g of active carbon and stirred at 20-25° C. for 30 minutes. The active carbon was filtered and washed with 10 mL of deionized water. The aqueous phases were combined and pH was adjusted to 3-4 with hydrochloric acid. The resulting mixture was extracted with 2×60 mL of ethyl acetate. The organic phases were combined and washed with 2×40 mL of deionized water. 40 mL of solvent were removed under vacuum. The resulting suspension was stirred at 20-25° C. for 30 minutes. The solid was filtered to yield 3.8 g of crude lifitegrast as a white solid. Purity (HPLC): 99.4%.

Example 17

Synthesis of Compound II 0.60 Kg of 1,1-carbonyldiimidazole and 13.1 Kg of ethyl acetate were added under nitrogen atmosphere. The mixture was stirred to complete dissolution and purified benzofuran-6-carboxylic acid (compound III) as obtained in Example 20 was added. In parallel, 1.82 Kg of benzyl (S)-2-(5,7-dichloro-1,2,3,4-tetrahydroisoquinoline-6-carboxamido)-3-[3-(methylsulfonyl)phenyl]propanoate (compound IV), 2.0 Kg of dimethylsulfoxide, 4.9 Kg of ethyl acetate and 0.94 Kg of N,N-diisopropylethylamine were mixed under nitrogen atmosphere. To the resulting mixture, it was added the solution of the activated benzofuran-6-carboxylic acid (activated compound III) and stirred for 18 h. Then, 16.4 Kg of ethyl acetate and 17.2 Kg of deionized water were added. pH was adjusted to below 4 with hydrochloric acid. The organic layer was extracted and washed with aqueous sodium bicarbonate and water. The resulting organic layer was treated with charcoal and filtered. The obtained solution was concentrated under vacuum and was then loaded over methyl tert-butyl ether. The resulting suspension was filtered and dried at 30° C. under vacuum to obtain 1.54 Kg of Compound II. HPLC (area %): 98.59%. GC: 7.59% methyl tert-butyl ether, 0.74% ethyl acetate.

Example 18

Synthesis of Lifitegrast 1.49 Kg of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) obtained as described in example 17, and 0.3 Kg of 5% palladium on charcoal (Johnson Matthey type 452) were suspended in 21.1 Kg of acetonitrile under nitrogen atmosphere. The mixture was cooled to 8° C. and 0.86 Kg (8.5 mol, 5 eq.) of trimethylamine and a solution of 0.29 Kg (6.3 mol, 3.7 eq.) of formic acid in 2.3 Kg of acetonitrile were added. The mixture was stirred at 8° C. while monitoring the content of dechlorinated impurities A and B by HPLC. The resulting suspension was filtered and the solvent was removed under vacuum. Then, 11.0 Kg of ethyl acetate and 26.8 Kg of water were added, and pH of the aqueous layer was adjusted to pH<3.0 with hydrochloric acid. The organic phase was extracted and washed with an aqueous solution of sodium bicarbonate. Unreacted benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) was recovered from the resulting organic phase as described in Example 19. The aqueous phase was washed with ethyl acetate, cooled to 0° C. and pH was adjusted with hydrochloric acid to below 3.5. The resulting suspension was filtered and the solid was purified by dissolving in aqueous sodium bicarbonate and subsequently neutralizing with hydrochloric acid. The resulting solid was dissolved in a mixture of 2.02 Kg of acetonitrile and 1.86 Kg of deionized water under heating. The solution was filtered and cooled to 20-25° C. The resulting suspension was filtered and the solid was purified by slurring in a mixture of 3.75 Kg of ethyl acetate and 5.85 Kg of methyl tert-butyl ether at reflux temperature. After cooling, the resulting suspension was filtered and the solid was dried at 40° C. in a vacuum oven. 480 g of Lifitegrast were obtained. Purity (HPLC): 99.50%. Sum of dechlorinated impurities A and B (HPLC, total area %): 0.20%.

Example 19

Recovery of Unreacted Compound II

The ethyl acetate solution containing 0.3 Kg of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II) as obtained in Example 18 was concentrated under reduced pressure. The resulting solution was added over 12 Kg of methyl tert-butyl ether. The resulting suspension was filtered and the obtained solid was dried at 30° C. under vacuum to obtain 0.27 Kg of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (compound II). HPLC (area %): 98.87%.

Example 20

Purification of Benzofuran-6-carboxylic Acid (Compound III)

A mixture of 40 g of benzofuran-6-carboxylic acid (compound III, HPLC area %: 99.80%), 68 mL of n-butyl acetate and 180 mL of water was heated to reflux. The mixture was then cooled to 0-5° C. and filtered. The resulting solid was suspended in n-butyl acetate. The obtained suspension was stirred overnight at reflux temperature and then cooled and filtered. The resulting solid was dried at 45° C. under vacuum to obtain 33.74 g of purified benzofuran-6-carboxylic acid (compound III). HPLC (area %): 99.89%.

Example 21

Synthesis of Lifitegrast

A mixture of 1.00 g of benzyl (S)-2-[2-(benzofuran-6-carbonyl)-5,7-dichloro-1,2,3,4-tetrahydroisoquinoline-6-carboxamido]-3-[3-(methylsulfonyl)phenyl]propanoate (Compound II), 0.10 g of 10% palladium on charcoal (Johnson Matthey type 487), 20 mL of acetonitrile, 0.40 g of triethylamine (2 eq.) and 0.06 g of formic acid were stirred overnight at 20-25° C. The resulting suspension was analyzed by HPLC. Conversion of Compound II into Lifitegrast: 80%. Sum of dechlorinated impurities A and B: 0.14% (HPLC, total area %).

The invention claimed is:

1. A process for preparing lifitegrast or a salt thereof, the process comprising hydrogenation of compound II

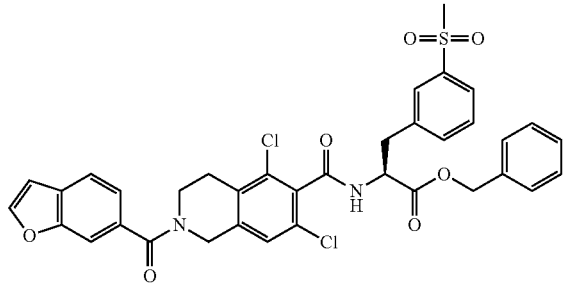

in a mixture comprising at least one solvent selected from the group consisting of acetonitrile, a ketone solvent, an ester solvent and a mixture thereof.

2. The process according to claim 1, wherein the hydrogenation is a transfer hydrogenolysis catalyzed by palladium and in the presence of formic acid or a salt thereof as a hydrogen donor.

3. The process according to claim 2, wherein the hydrogen donor is triethylammonium formate.

4. The process according to claim 1, wherein the ketone solvent is selected from the group consisting of acetone, methyl butyl ketone, methyl ethyl ketone, methyl isobutyl ketone, methyl isopropyl ketone and a mixture thereof, and the ester solvent is selected from the group consisting of butyl acetate, ethyl acetate, ethyl formate, isobutyl acetate, isopropyl acetate, methyl acetate, methyl formate, propyl acetate and a mixture thereof.

5. The process according to claim 1, wherein the hydrogenation is performed in the presence of a chloride salt.

6. The process according to claim 5, wherein the chloride salt is an ammonium chloride salt.

7. The process according to claim 1, wherein the process comprises:

(a) reacting compound III

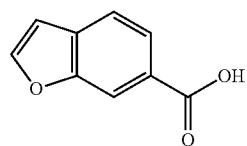

or a salt thereof with 1,1'-carbonyldiimidazole (CDI) to obtain an activated derivative of compound III; and (b) reacting the activated derivative of compound III of step (a) with compound IV

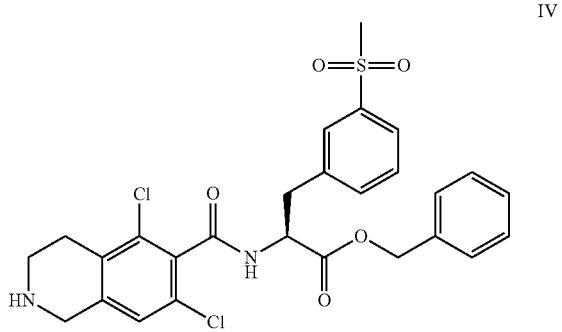 [SMILES: CS(=O)(=O)c1cccc(C[C@H](NC(=O)c2c(Cl)cc3c(c2Cl)CCNC3)C(=O)OCc2ccccc2)c1]

or a salt thereof, to obtain compound II

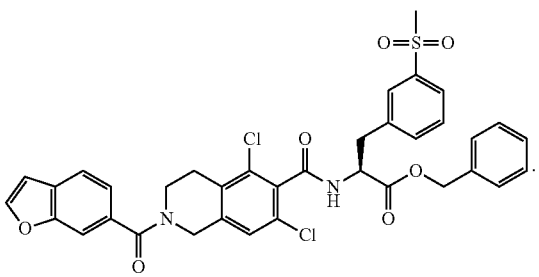

8. The process according to claim 7, wherein the reaction to obtain compound II is performed in a solvent selected from the group consisting of butyl acetate, ethyl acetate, ethyl formate, isobutyl acetate, isopropyl acetate, methyl acetate, methyl formate, propyl acetate, dimethylsulfoxide, N,N-dimethylformamide, N,N-dimethylacetamide and a mixture thereof.

9. The process according to claim 7, wherein the process comprises deprotecting the compound of formula V

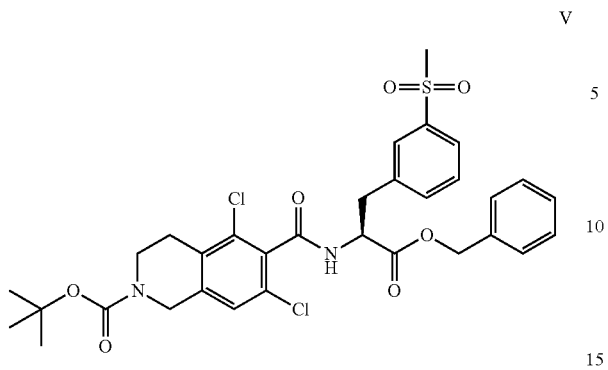

to obtain compound IV

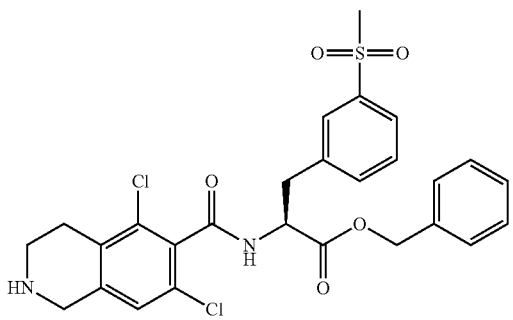

or a salt thereof.

10. The process according to claim 9, wherein the deprotection is performed using hydrogen chloride and in a solvent selected from the group consisting of butyl acetate, ethyl acetate, ethyl formate, isobutyl acetate, isopropyl acetate, methyl acetate, methyl formate, propyl acetate and a mixture thereof.

11. The process according to claim 9, wherein the process comprises:

(c) reacting compound VII

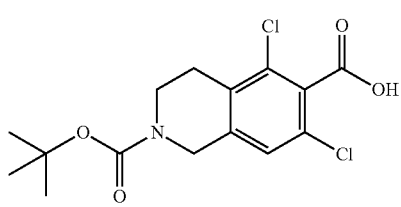

or a salt thereof with oxalyl chloride to obtain an activated derivative of compound VII; and (d) reacting the activated derivative of compound VII of step (c) with compound VI

or a salt thereof, to obtain compound V

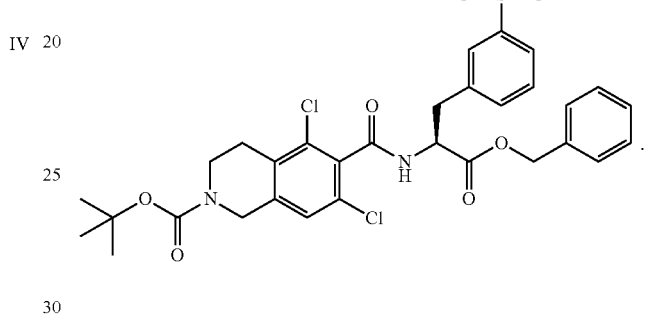

12. The process according to claim 11, wherein the reaction to obtain compound V is performed in a solvent selected from the group consisting of butyl acetate, ethyl acetate, ethyl formate, isobutyl acetate, isopropyl acetate, methyl acetate, methyl formate, propyl acetate, dimethylsulfoxide, NN-dimethylformamide, N,N-dimethylacetamide and a mixture thereof.

13. The process according to claim 1, wherein the hydrogenation is a transfer hydrogenolysis catalyzed by palladium and in the presence of formic acid or a salt thereof as a hydrogen donor; and the ketone solvent is selected from the group consisting of acetone, methyl butyl ketone, methyl ethyl ketone, methyl isobutyl ketone, methyl isopropyl ketone and a mixture thereof, and the ester solvent is selected from the group consisting of butyl acetate, ethyl acetate, ethyl formate, isobutyl acetate, isopropyl acetate, methyl acetate, methyl formate, propyl acetate and a mixture thereof.

14. The process according to claim 13, wherein the hydrogen donor is triethylammonium formate.

15. The process according to claim 14, wherein the hydrogenation is performed in the presence of a chloride salt.

16. The process according to claim 1, wherein the hydrogenation is a transfer hydrogenolysis catalyzed by palladium and in the presence of formic acid or a salt thereof as a hydrogen donor; and the hydrogenation is performed in the presence of a chloride salt.

17. The process according to claim 9, wherein the deprotection is performed using hydrogen chloride and in a solvent selected from the group consisting of butyl acetate, ethyl acetate, ethyl formate, isobutyl acetate, isopropyl acetate, methyl acetate, methyl formate, propyl acetate and a mixture thereof; and the process comprises:

(c) reacting compound VII

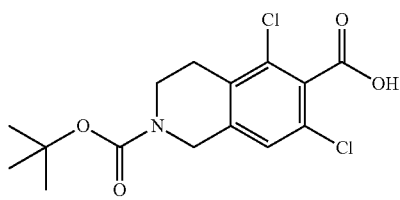

or a salt thereof with oxalyl chloride to obtain an activated derivative of compound VII; and (d) reacting the activated derivative of compound VII of step (c) with compound VI

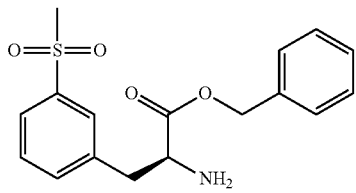

or a salt thereof, to obtain compound V

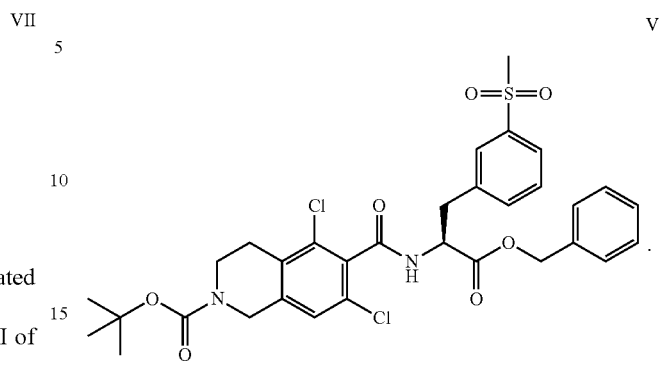

18. The process according to claim 1, wherein the mixture of at least one solvent for hydrogenation of compound II comprises acetonitrile.

19. The process according to claim 6, wherein the ammonium chloride salt is tetrabutylammonium chloride.

20. The process according to claim 8, wherein the solvent for the reaction to obtain compound II is a mixture comprising ethyl acetate and dimethylsulfoxide.

* * * * *